United States Patent [19]

Matoba et al.

[11] Patent Number: 4,983,836
[45] Date of Patent: Jan. 8, 1991

[54] METHOD FOR DETECTING THINNED OUT PORTION ON INNER SURFACE OR OUTER SURFACE OF PIPE

[75] Inventors: Yuji Matoba; Toshio Koshihara, both of Tokyo, Japan

[73] Assignee: NKK Corporation, Tokyo, Japan

[21] Appl. No.: 364,011

[22] Filed: Jun. 9, 1989

[30] Foreign Application Priority Data

Jun. 30, 1988 [JP] Japan ................................ 63-163550
Jun. 30, 1988 [JP] Japan ................................ 63-163551
Aug. 24, 1988 [JP] Japan ................................ 63-210080

[51] Int. Cl.$^5$ ............................................... G01J 5/02
[52] U.S. Cl. ................................... 250/330; 250/332; 250/334
[58] Field of Search ...................... 250/330, 332, 334

[56] References Cited

U.S. PATENT DOCUMENTS

| 4,218,707 | 8/1980 | Reed et al. ................. | 250/334 X |
| 4,468,136 | 8/1984 | Murphy et al. ............. | 250/334 X |
| 4,644,162 | 2/1987 | Bantel et al. ............... | 250/334 X |
| 4,647,220 | 3/1987 | Adams et al. .............. | 250/330 X |
| 4,872,762 | 10/1989 | Koshihara et al. ......... | 250/330 X |
| 4,886,370 | 12/1989 | Koshihara et al. ......... | 250/330 X |

Primary Examiner—Constantine Hannaher
Assistant Examiner—Jacob Eisenberg
Attorney, Agent, or Firm—Frishauf, Holtz, Goodman & Woodward

[57] ABSTRACT

A method for detecting a thinned out portion on the inner surface or the outer surface of a pipe, comprising heating or cooling a pipe to be tested from the outer surface or the inner surface thereof so that a difference in temperature is produced between two portions of the outer surface or the inner surface of the pipe corresponding to a thinned out portion and a normal portion of the inner surface or the outer surface of the pipe; shooting the outer surface or the inner surface of the pipe by means of a thermal imaging system to obtain a thermal image of the difference in temperature; and then calculating a differential value of a temperature distribution of the thermal image of the difference in temperature on a line passing the highest temperature point or the lowest temperature point in the thermal image of the difference in temperature. Then, two points of inflection are determined on both sides of the highest temperature point or the lowest temperature point of the temperature distribution for the thinned out portion, on the basis of the differential value of the temperature distribution; and then an extent of the thinned out portion is detected on the basis of a distance between the two points of inflection of the temperature distribution.

10 Claims, 8 Drawing Sheets

DISTANCE FROM CENTER OF THINNED OUT PORTION (mm)

DISTANCE FROM CENTER OF THINNED OUT PORTION (mm)

METHOD FOR DETECTING THINNED OUT PORTION ON INNER SURFACE OR OUTER SURFACE OF PIPE

FIELD OF THE INVENTION

The present invention relates to a method for detecting a thinned out portion as a defective portion existing on the inner surface or the outer surface of a pipe.

BACKGROUND OF THE INVENTION

On the inner surface of a pipe, the outer surface of which is exposed, installed on the ground for transporting, for example, a fluid such as a gas or a liquid, or on the outer surface of a pipe, the outer surface of which is not exposed, installed under the ground, a thinned out portion caused by corrosion or the like may be present.

Presence of a thinned out portion as the defective portion as mentioned above on the inner surface or the outer surface of the Pipe ultimately results in such problems as production of a hole at the thinned out portion. It is therefore necessary to promptly detect the above-mentioned thinned out portion on the inner surface or the outer surface of the Pipe, and replace the pipe having such a thinned out portion with new one.

The following methods are known for detecting a thinned out portion as a defective portion on the inner surface of a pipe, the outer surface of which is exposed:

(1) Detecting method using radioactive rays:

This method comprises projecting radioactive rays such as X-ray or gamma-ray toward a pipe to be tested from the side of the outer surface thereof, measuring the amount of radioactive rays having passed through the pipe, and detecting a thinned out portion on the inner surface of the pipe by means of the amount of transmission of the radioactive rays.

(2) Detecting method using ultrasonic waves:

This method comprises transmitting ultrasonic waves toward a pipe to be tested from the side of the outer surface thereof, receiving reflected waves of the transmitted ultrasonic waves, measuring the time required up to receiving of the reflected waves, and detecting a thinned out portion on the inner surface of the pipe by means of the time required up to receiving of the reflected waves.

(3) Detecting method based on knocking:

This method comprises knocking a pipe to be tested from the side of the outer surface thereof with a hammer, for example, and detecting a thinned out portion on the Inner surface of the pipe by means of the thus produced sound.

(4) Detecting method based on cutting:

This method comprises cutting a pipe to be tested to permit an operator to directly observe the inner surface of the pipe, thereby detecting a thinned out portion on the inner surface of the pipe.

The following method is known for detecting a thinned out portion as a defective portion on the outer surface of a pipe, the outer surface of which is not exposed: (5) Detecting method using ultrasonic waves:

This method comprises transmitting ultrasonic waves toward a pipe to be tested from the side of the inner surface thereof, receiving reflected waves of the transmitted ultrasonic waves, measuring the time required up to receiving of the reflected waves, and detecting a thinned out portion on the outer surface of the pipe by means of the time required up to receiving of the reflected waves.

The detecting method using radioactive rays as mentioned in (1) above has the following problems:

(a) The detecting operation of a thinned out portion cannot be conducted unless the operator is qualified for handling radioactive rays. There is therefore a limitation in personnel.

(b) It is difficult to make a proper judgement on the result of detection, requiring high-level experience and technical knowledge.

(c) The detecting operation of a thinned out portion can be carried out only at a position closest to the outer surface of the pipe. When the pipe is installed at an elevated position apart from the ground, therefore, it is necessary to provide a scaffold for the detecting operation.

(d) The range of a single run of detection is narrow. It thus requires much time and labor for the detecting operation, leading to a low operating efficiency.

The detecting method using ultrasonic waves as mentioned in (2) and (5) above has the following problems:

(a) An error is often contained in the result of detection of a thinned out portion, thus preventing accurate detection.

(b) It is difficult to detect an extent and/or a depth of a thinned out portion.

(c) The range of a single run of detection, being only a point, is very narrow. It thus requires much time and labor for the detecting operation, leading to a low operating efficiency.

The detecting method based on knocking as mentioned in (3) above has the following problems:

(a) Determination of the presence of a thinned out portion requires high-level experience and technical knowledge, with furthermore much differences between individual operators, thus impairing accurate detection of the thinned out portion.

(b) It is impossible to detect an extent and/or a depth of a thinned out portion, and it is difficult to detect a small thinned out portion.

(c) The detecting operation of a thinned out portion can be carried out only at a position closest to the outer surface of the pipe. When the pipe is installed at an elevated position apart from the ground, therefore, it is necessary to provide a scaffold for the detecting operation.

(d) The detecting operation requires much time and labor, resulting in a low operating efficiency.

The detecting method based on cutting as mentioned in (4) above has the following problems:

(a) Use of the pipe must be interrupted for a while during cutting and detecting operations of a thinned out portion, and these cutting, detecting and restoring operations require much time and labor, resulting in a low operating efficiency.

(b) When the pipe is installed at an elevated position apart from the ground, it is necessary to provide a scaffold for the detecting operation.

Under such circumstances, there is a strong demand for the development of a method which permits certain, easy and efficient detection of the presence of a thinned out portion as a defective portion and an extent and/or a depth thereof, on the inner surface or the outer surface of a pipe, without the need for a special qualification, but a method provided with such properties has not as yet been proposed.

SUMMARY OF THE INVENTION

An object of the present invention is therefore to provide a method which permits certain, easy and efficient detection of the presence of a thinned out portion as a defective portion and an extent and/or a depth thereof, on the inner surface or the outer surface of a pipe, without the need for a special qualification.

In accordance with one of the features of the present invention, there is provided a method for detecting a thinned out portion on the inner surface or the outer surface of a pipe, characterized by comprising the steps of:

heating or cooling a pipe to be tested from the side of the outer surface thereof or the inner surface thereof so that a difference in temperature is produced between a portion of the outer surface or the inner surface of said pipe corresponding to a thinned out portion as a defective portion on the inner surface or the outer surface of said pipe, on the one hand, and a portion of the outer surface or the inner surface of said pipe corresponding to a normal portion of the inner surface or the outer surface of said pipe, on the other hand; then shooting the outer surface or the inner surface of said pipe by means of a thermal imaging system while said difference in temperature still remains on the outer surface or the inner surface of said pipe, to obtain a thermal image of said difference in temperature; then detecting said thinned out portion on the inner surface or the outer surface of said pipe by means of the thus obtained thermal image;

determining a temperature distribution of said thermal image of said difference in temperature on a line passing the highest temperature point or the lowest temperature point in said thermal image of said difference in temperature; then calculating a differential value of said temperature distribution; then determining two points of inflection on both sides of said highest temperature point or said lowest temperature point of said temperature distribution for said thinned out portion, on the basis of said calculated differential value of said temperature distribution; and then detecting an extent of said thinned out portion on the basis of a distance between said two points of inflection of said temperature distribution.

DETAILED DESCRIPTION OF PREFERRED EMBODIMENTS

From the above-mentioned point of view, extensive studies were carried out to develop a method which permits certain, easy and efficient detection of the presence of a thinned out portion as a defective portion and an extent and/or a depth thereof, on the inner surface or the outer surface of a pipe, without the need for a special qualification. As a result, the following finding was obtained:

For example, a pipe to be tested is heated or cooled for a certain period of time from the side of the outer surface thereof or the inner surface thereof. If there is a thinned out portion as a defective portion on the inner surface of the pipe, this thinned out portion has a smaller thermal capacity than that of a normal portion of the pipe. A difference in temperature is therefore produced between a portion of the outer surface of the pipe corresponding to the thinned out portion on the inner surface thereof, on the one hand, and a portion of the outer surface of the pipe corresponding to the normal portion of the inner surface of the pipe, on the other hand. By shooting the outer surface of the pipe while this difference in temperature still remains on the outer surface of the pipe by means of a thermal imaging system, a thermal image of the difference in temperature described above is obtained. Then, a temperature distribution of the thermal image of the difference in temperature on a line passing the highest temperature point or the lowest temperature point in the thus obtained thermal image is determined. Subsequently, a differential value of the thus determined temperature distribution is calculated, and two points of inflection on the both sides of the highest temperature point or the lowest temperature point of the temperature distribution for the thinned out portion, are determined on the basis of the thus calculated differential value of the temperature distribution. The presence of the thinned out portion and the extent thereof can thus be detected on the basis of a distance between the two points of inflection.

The present invention was developed on the basis of the aforementioned finding. Now, the method of the present invention is described below with reference to the drawings as to a case of detection of the presence of a thinned out portion as a defective portion and an extent and/or a depth thereof, on the inner surface of a pipe, the outer surface of which is exposed.

Figure 1:
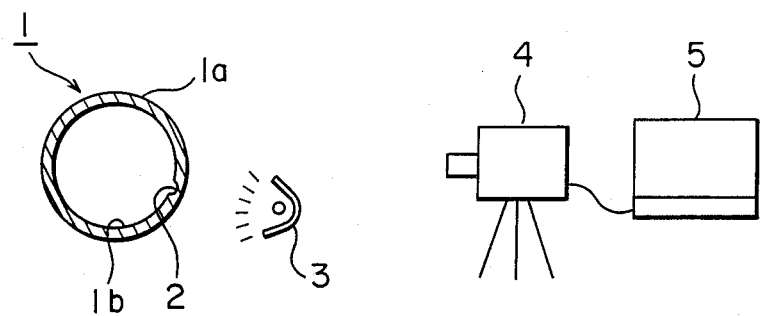
FIG. 1 is a schematic descriptive side view illustrating the method of the present invention.

FIG. 1 is a schematic descriptive side view illustrating a first embodiment of the method of the present invention. As shown in FIG. 1, a pipe 1 to be tested, the outer surface 1a of which is exposed, is heated from the side of the outer surface 1a thereof by means of a heating mechanism 3 so that a difference in temperature is produced between a portion of the outer surface 1a of the pipe 1 corresponding to a thinned out portion 2 as a defective portion on the inner surface 1b thereof, on the one hand, and a portion of the outer surface 1a of the pipe 1 corresponding to a normal portion of the inner surface 1b thereof, on the other hand.

The thinned out portion 2 on the inner surface 1b of the pipe 1 has a thermal capacity smaller than that of the normal portion of the pipe 1. The temperature of the portion of the outer surface 1a of the pipe 1 corresponding to the thinned out portion 2 on the inner surface 1b of the pipe 1 therefore increases, by means of the above-mentioned heating, more rapidly than that of the portion of the outer surface 1a of the pipe 1 corresponding to the normal portion of the inner surface 1b thereof. As a result, during the period of time from the beginning to the end of heating and during a certain period of time after the end of heating, the temperature of the portion of the outer surface 1a corresponding to the thinned out portion 2 on the inner surface 1b becomes higher than the temperature of the portion of the outer surface 1a corresponding to the normal portion of the inner surface 1b, thus producing a difference in temperature between these portions.

Figure 2:
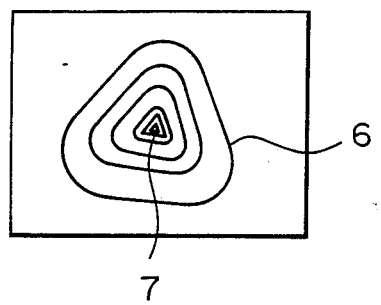
FIG. 2 is a descriptive view illustrating a typical thermal image of a difference in temperature, which shows a thinned out portion and its surroundings, as shot in accordance with the method of the present invention.

While the above-mentioned difference in temperature still remains on the outer surface 1a of the pipe 1, the outer surface 1a of the pipe 1 is shot by means of a thermal imaging system 4 to obtain a thermal image of the difference in temperature, which has a portion showing a higher temperature corresponding to the thinned out portion 2 on the inner surface 1b of the pipe 1. The thus obtained thermal image of the difference in temperature is displayed on a monitor TV screen 5. FIG. 2 is a descriptive view illustrating a typical thermal image of the difference in temperature shot as described above. As shown in FIG. 2, in the thermal image 6 of the difference in temperature showing the thinned out portion 2 on the inner surface 1b of the Pipe 1, the individual ranges of temperature are indicated by respective predetermined colors. The highest temperature point 7 in the thermal image 6 represents the deepest point, i.e., the center of the thinned out portion 2.

Figure 3:
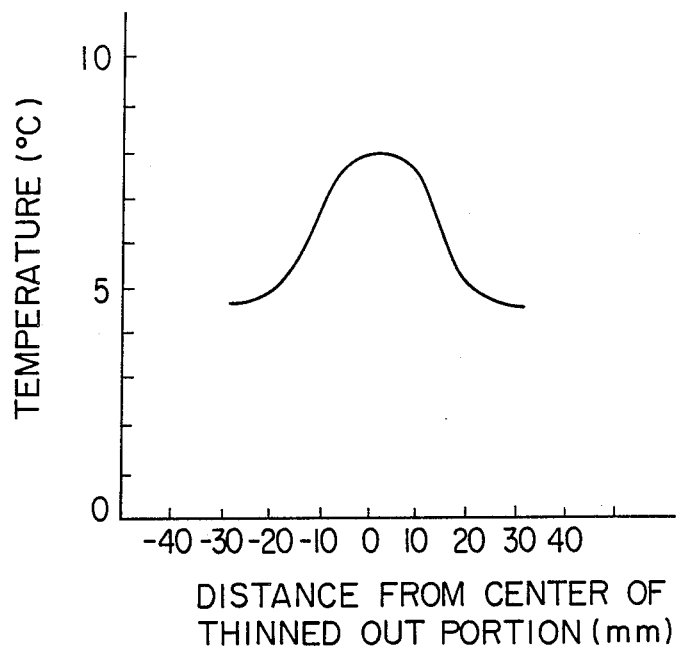
FIG. 3 is a graph illustrating a typical temperature distribution of a thermal image of the difference in temperature on a line passing the highest temperature point in the thermal image of the difference in temperature, which shows a thinned out portion, as determined in accordance with the method of the present invention.

Then, there is determined a temperature distribution of the thermal image 6 of the difference in temperature on a line passing the highest temperature point 7 in the thermal image 6 of the difference in temperature showing the thinned out portion 2. FIG. 3 is a graph illustrating a typical temperature distribution of a thermal image of the difference in temperature thus determined. In FIG. 3, the ordinate represents the temperature, and the abscissa represents the distance from the center of the thinned out portion 2. As is clear from FIG. 3, the temperature distribution of the difference in temperature of the thermal image 6 is represented by a curve in which the temperature gradually decreases from the center showing the highest temperature of the thinned out portion toward the periphery thereof.

Figure 5:
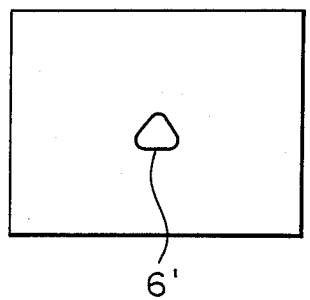
FIG. 5 is a descriptive view illustrating a typical thermal image of a difference in temperature, which shows only a thinned out portion, as shot in accordance with the method of the present invention.
Figure 4:
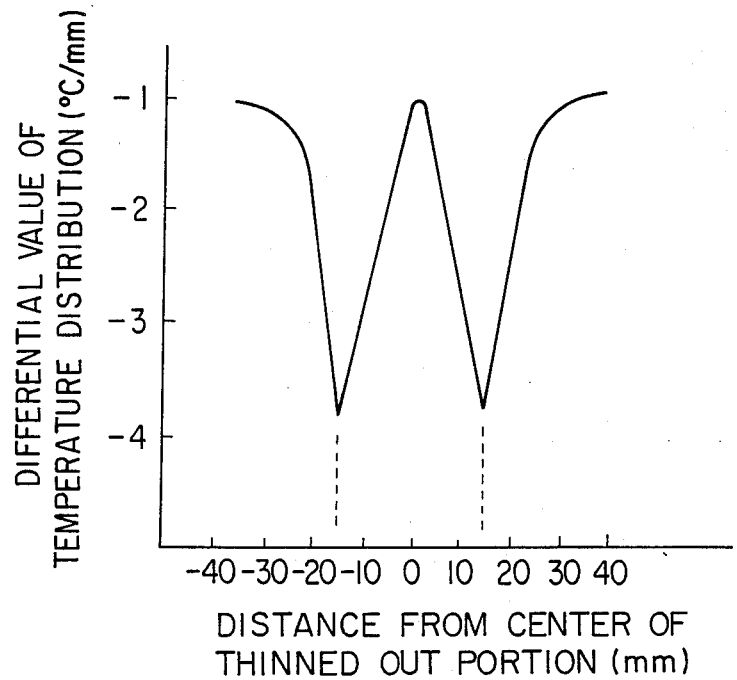
FIG. 4 is a graph illustrating a differential value of a temperature distribution of a thermal image, as calculated in accordance with the method of the present invention.

Subsequently, a differential value of the temperature distribution of the thermal image shown in FIG. 3 is calculated, and two points of inflection on the both sides of the highest temperature point of the temperature distribution are determined for the thinned out portion 2, on the basis of the thus calculated differential value of the temperature distribution. It is thus possible to detect the presence and the extent of the thinned out portion 2 on the basis of a distance between the thus determined two points of inflection of the temperature distribution. FIG. 4 is a graph illustrating the above-mentioned differential value of the temperature distribution of the thermal image. In FIG. 4, the ordinate represents the differential value of the temperature distribution, and the abscissa represents the distance from the center of the thinned out portion. As is clear from FIG. 4, the two points of inflection on the both sides of the highest temperature point of the temperature distribution are situated respectively at a distance of 15 mm from the center of the thinned out portion. There is therefore a distance of 30 mm between the two points of inflection. As a result, the presence of a thinned out portion having a diameter of 30 mm on the inner surface 1b of the pipe 1 is detected. FIG. 5 is a descriptive view illustrating the thermal image 6' of the difference in temperature, which shows only the thus detected thinned out portion.

The heating mechanism 3 shown in FIG. 1 should preferably be one capable of rapidly heating the pipe 1 in a short period of time such as an infrared heater. When heating the pipe 1 from the side of the outer surface 1a thereof by means of the heating mechanism 3 and shooting the outer surface 1a of the pipe 1 by means of the thermal imaging system 4, it is necessary to heat the pipe 1 from the side of the outer surface 1a thereof during such a period of time as to produce the above-mentioned difference in temperature between the portion of the outer surface 1a of the pipe 1 corresponding to the thinned out portion 2 on the inner surface 1b of the pipe 1, on the one hand, and the portion of the outer surface 1a of the pipe 1 corresponding to the normal portion of the inner surface 1b of the pipe 1, on the other hand, and to shoot the outer surface 1a of the pipe 1 by means of the thermal imaging system 4 while the above-mentioned difference in temperature still remains on the outer surface 1a of the pipe 1. The difference in temperature almost disappear if the period of time for heating or the period of time from the end of heating up to shooting exceed a certain period of time, thus making it impossible to detect the thinned out portion 2 on the inner surface 1b of the pipe 1. The above-mentioned heating of the pipe 1 may be carried out from the side of the inner surface 1b of the pipe 1.

In place of heating of the pipe 1 from the side of the outer surface 1a thereof or the inner surface 1b thereof, the pipe 1 may be cooled from the side of the outer surface 1a thereof or the inner surface 1b thereof. Cooling of the pipe 1 from the side of the outer surface 1a thereod or from the side of the inner surface 1b thereof is accomplished by spraying a cooling medium onto the outer surface 1a or the inner surface 1b of the pipe 1 by means of a cooling mechanism not shown. An applicable cooling medium includes water and air as well as a liquefied gas and a low-boiling-point liquid.

When cooling the pipe 1 from the side of the outer surface 1a thereof or from the inner surface 1b thereof, the presence of the thinned out portion 2 as the defective portion and the extent thereof, on the inner surface 1b of the pipe 1, are detected as follows.

The thinned out portion 2 on the inner surface 1b of the pipe 1 has a thermal capacity smaller than that of the normal portion of the pipe 1, as described above. Therefore, the temperature of the portion of the outer surface 1a of the pipe 1 corresponding to the thinned out portion 2 on the inner surface 1b of the pipe 1 decreases, by means of the above-mentioned cooling, more rapidly than that of the portion of the outer surface 1a of the pipe 1 corresponding to the normal portion of the inner surface 1b thereof. As a result, during the period of time from the beginning to the end of cooling and during a certain period of time after the end of cooling, the temperature of the portion of the outer surface 1a corresponding to the thinned out portion 2 on the inner surface 1b becomes lower than the temperature of the portion of the outer surface 1a corresponding to the normal portion of the inner surface 1b, thus producing a difference in temperature between these portions.

While the above-mentioned difference in temperature still remains on the outer surface 1a of the pipe 1, the outer surface 1a of the pipe 1 is shot by means of the thermal imaging system 4 to obtain a thermal image of the difference in temperature, which has a portion showing a lower temperature corresponding to the thinned out portion 2 on the inner surface 1b of the pipe 1. Then, there is determined a temperature distribution of the thermal image of the difference in temperature on a line passing the lowest temperature point in the thermal image of the difference in temperature showing the thinned out portion 2. Subsequently, a differential value of the temperature distribution of the thermal image is calculated, and two points of inflection on the both sides of the lowest temperature point of the temperature distribution are determined for the thinned out portion 2, on the basis of the thus calculated differential value of the temperature distribution. It is thus possible to detect the presence and the extent of the thinned out portion 2 on the basis of a distance between the thus determined two points of inflection of the temperature distribution.

According to the method of the present invention, it is possible, as required, to detect the depth of a thinned out portion, in addition to the extent of the thinned our portion described above. A second embodiment of the method of the present invention is described below with reference to the drawings as to a case of detection of the extent and the depth of a thinned out portion as a defective portion existing on the inner surface of a pipe are detected.

The presence of a thinned out portion 2 and the extent thereof on the inner surface 1b of the pipe 1 are detected in accordance with the first embodiment of the method of the present invention described above. On the other hand, an experimental pipe having an artificial thinned out portion of a prescribed extent and a prescribed depth on the inner surface thereof is heated or cooled from the side of the outer surface thereof or the inner surface thereof, to previously determine a heat analysis data concerning the relationship between the highest temperature or the lowest temperature of a portion of the outer surface of the experimental pipe corresponding to the artificial thinned out portion on the inner surface of the experimental pipe, an extent of the artificial thinned out portion, and a depth of the artificial thinned out portion.

Figure 6:
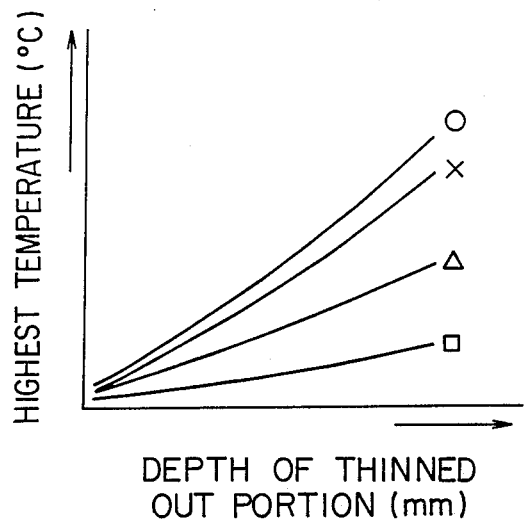
FIG. 6 is a graph illustrating a typical heat analysis data as determined in accordance with the method of the present invention.

FIG. 6 is a graph illustrating a typical heat analysis data determined by heating an experimental pipe having an artificial thinned out portion of a prescribed extent and a prescribed depth on the inner surface thereof from the side of the outer surface thereof or the inner surface thereof. In FIG. 6, the ordinate represents the highest temperature of the portion of the outer surface of the experimental pipe corresponding to the artificial thinned out portion on the inner surface of the experimental pipe, and the abscissa represents the depth of the artificial thinned out portion of the experimental pipe. In FIG. 6, the curves "o", "x", "Δ" and "☐" represent the highest temperature of the portion of the outer surface of the experimental pipe corresponding to the artificial thinned out portion for each of various extents of the thinned out portion on the inner surface of the experimental pipe, in relation to the depth of the artificial thinned out portion. More specifically, the curve "o" represents a case with the smallest extent of the artificial thinned out portion; and the curves "x" "Δ" and "☐" represent cases with larger extents of the artificial thinned out portions in this order. The above-mentioned heat analysis data is previously determined for each of various conditions of the pipe to be tested and the thinned out portion as a defective portion, such as the wall thickness of the pipe to be tested, the approximate shape of the thinned out portion as the defective portion, and the presence of a fluid flowing through the pipe to be tested.

As shown in FIG. 3, the highest temperature point in the thermal image is already detected from the temperature distribution of the thermal image of the difference in temperature, which shows the thinned out portion 2 on the inner surface 1b of the pipe 1 to be tested. Also, the extent of the thinned out portion 2 is already detected from the distance between the two points of inflection on the both sides of the highest temperature point of the above-mentioned temperature distribution, as shown in FIG. 4. It is therefore possible to detect the depth of the thinned out portion 2, on the basis of the detected highest temperature point in the thermal image, the detected extent of the thinned out portion 2 and the previously determined heat analysis data.

When the thinned out portion 2 is detected by cooling the pipe 1 from the side of the outer surface 1a thereof or the inner surface 1b thereof, it is necessary that an experimental pipe having an artificial thinned out portion of a prescribed extent and a prescribed depth on the inner surface thereof is cooled from the side of the outer surface thereof or the inner surface thereof, to previously determine a heat analysis data concerning the relationship between the lowest temperature of the portion of the outer surface of the experimental pipe corresponding to the artificial thinned out portion on the inner surface of the experimental pipe, an extent of the artificial thinned out portion, and a depth of the artificial thinned out portion.

According to the first or the second embodiment of the method of he present invention, it is possible not only to detect a thinned out portion existing on the inner surface of a pipe, the outer surface of which is exposed, as described above, but also to detect the presence of a thinned out portion as a defective portion and an extent and/or a depth thereof, on the outer surface not exposed of a pipe installed under the ground for transporting, for example, a fluid such as a gas or a liquid.

The presence of a thinned out portion as a defective portion and an extent and/or a depth thereof on the outer surface of a pipe, the outer surface of which is not exposed, are detected as follows.

A pipe to be tested, the outer surface of which is not exposed, is heated or cooled from the side of the inner surface thereof so that a difference in temperature is produced between a portion of the inner surface of the pipe corresponding to a thinned out portion as a defective portion on the outer surface of the pipe, on the one hand, and a portion of the inner surface of the pipe corresponding to a normal portion of the outer surface thereof, on the other hand. Then, while the above-mentioned difference in temperature still remains on the inner surface of the pipe, the inner surface of the pipe is shot by means of a thermal imaging system to obtain a thermal image of the difference in temperature showing the thinned out portion on the outer surface of the pipe. Then, there is determined a temperature distribution of the thermal image of the difference in temperature on a line passing the highest temperature point or the lowest temperature point in the thermal image of the difference in temperature showing the thinned out portion. Subsequently, a differential value of the temperature distribution of the thermal image is calculated, and two points of inflection on the both sides of the highest temperature point or the lowest temperature point of the temperature distribution are determined for the thinned out portion, on the basis of the thus calculated differential value of the temperature distribution. It is thus possible to detect the presence and the extent of the thinned out portion on the basis of a distance between the thus determined two points of inflection of the temperature distribution.

On the other hand, an experimental pipe having an artificial thinned out portion of a prescribed extent and a prescribed depth on the outer surface thereof is heated or cooled from the side of the inner surface thereof, to previously determine a heat analysis data concerning the relationship between the highest temperature or the lowest temperature of a portion of the inner surface of the experimental pipe corresponding to the artificial thinned out portion on the outer surface of the experimental pipe, an extent of the artificial thinned out portion, and a depth of the artificial thinned out portion. The depth of the thinned out portion as the defective portion is thus detected on the basis of the detected highest temperature point or the lowest temperature point in the thermal image, the detected extent of the thinned out portion and the previously determined heat analysis data.

When detecting the presence of a thinned out portion as a defective portion and an extent and/or a depth thereof on the inner surface or the outer surface of a pipe in accordance with the first or the second embodiment of the method of the present invention as described above, emissivity of the outer surface or the inner surface of the pipe exerts an influence on the thermal image of the difference in temperature obtained by means of a thermal imaging system. For example, when an adhesion of foreign matters such as rust or dirt, or a thinned out portion such as flaws is present on the outer surface of the pipe, and the pipe is heated from the side of the outer surface thereof, and then the outer surface of the pipe is shot by means of a thermal imaging system, the thus obtained thermal image of the difference in temperature of the outer surface of the pipe, includes a thermal image showing the adhesion of foreign matters or the thinned out portion as mentioned above, i.e., a pseudo defective portion on the outer surface of the pipe, in addition to a thermal image showing a thinned out portion as a defective portion on the inner surface of the pipe. Therefore, unless the thermal image showing the pseudo defective portion as mentioned above is eliminated from the thermal image obtained by means of the thermal imaging system, the thermal image showing only the thinned out portion as the defective portion cannot be obtained.

In the method of the present invention, therefore, prior to detecting the presence of the thinned out portion as the defective portion and the extent and/or the depth thereof, as required, the thermal image showing the above-mentioned pseudo defective portion existing on the outer surface or the inner surface of the pipe is eliminated from the thermal image obtained by means of the thermal imaging system.

A third embodiment of the method of the present invention is described below with reference to the drawings as to a case in which the thermal image showing a pseudo defective portion existing on the outer surface of a pipe, the outer surface of which is exposed, is first eliminated from the thermal image of the difference in temperature obtained by means of the thermal imaging system, and then the presence of a thinned out portion as a defective portion and an extent and/or a depth thereof on the inner surface of the pipe is detected.

Figure 7A:
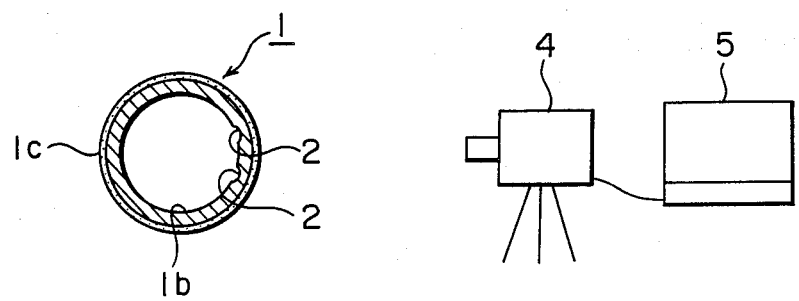
FIGS. 7(a) and 7(b) are schematic descriptive side views illustrating a case where a thinned out portion existing on the inner surface of a pipe is detected, after elimination of a thermal image which shows a pseudo defective portion existing on the outer surface of the pipe, in accordance with the method of the present invention.
Figure 8:
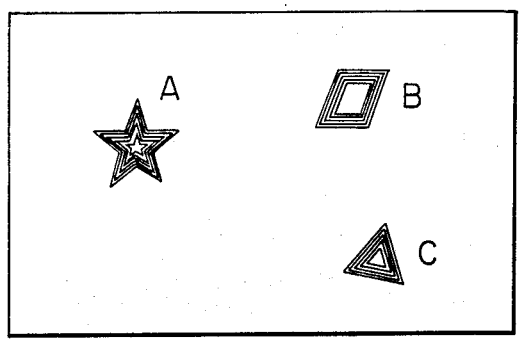
FIG. 8 is a diagrammatic view illustrating a thermal image of a difference in temperature, which shows a pseudo defective portion, as shot in accordance with the method of the present invention.

As shown in FIG. 7(A), prior to heating a pipe 1 having a paint film 1c on the outer surface thereof and having a thinned out portion 2 as a defective portion on the inner surface 1b thereof from the side of the outer surface thereof or the inner surface thereof, the outer surface having the paint film 1c thereon of the pipe 1 is shot by means of a thermal imaging system 4 to obtain a thermal image showing pseudo defective portions such as dirt or flaws on the paint film 1c. The thus obtained thermal image is displayed on a monitor TV screen 5. FIG. 8 is a diagrammatic view illustrating the thus obtained thermal image showing pseudo defective portions. In FIG. 8, "A" and "B" are portions of the thermal image, which show higher temperatures caused by dirt adhering onto the paint film 1c, and "C" is a portion of the thermal image, which shows a lower temperature caused by peeloff of the paint film 1c, i.e., caused by the exposure of the outer surface of the pipe 1. The thus obtained thermal image having the above-mentioned portions "A", "B" and "C", which show the pseudo defective portions, is processed by means of an image processor not shown to obtain thermal image signals, and the thus obtained thermal image signals are entered into a memory not shown such as a video tape or a floppy disk.

Figure 7B:
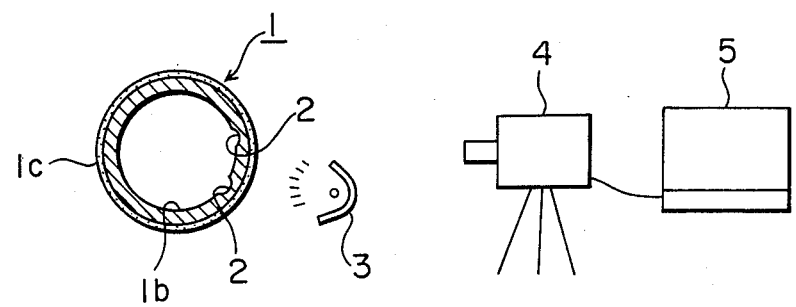
Figure 9:
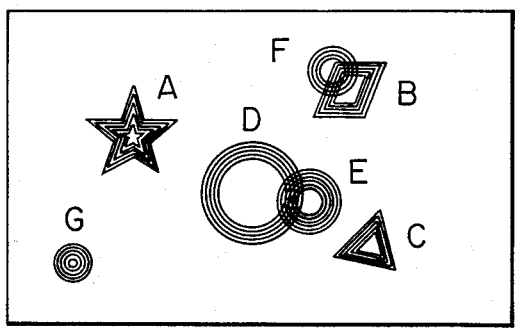
FIG. 9 is a diagrammatic view illustrating a thermal image of a difference in temperature, which shows a pseudo defective portion and a thinned out portion, as shot in accordance with the method of the present invention.

Then, the pipe 1 is heated from the side of the outer surface having the paint film 1c thereon of the pipe 1 by means of a heating mechanism 3 as shown in FIG. 7(B), so that a difference in temperature is produced between a portion of the outer surface of the pipe 1 corresponding to a thinned out portion 2 as a defective portion on the inner surface 1b of the pipe 1, on the one hand, and a portion of the outer surface of the pipe 1 corresponding to a normal portion of the inner surface 1b of the pipe 1, on the other hand. Then, while the above-mentioned difference in temperature still remains on the outer surface of the pipe 1, the outer surface of the pipe 1 is shot by means of the thermal imaging system 4 to obtain a thermal image of the difference in temperature, which has a portion showing a higher temperature corresponding to the thinned out portion 2 on the inner surface 1b of the pipe 1. The thus obtained thermal image of the difference in temperature is displayed on a monitor TV screen 5. FIG. 9 is a diagrammatic view illustrating the thus obtained thermal image of the difference in temperature, which shows pseudo defective portions and thinned out portions.

Figure 10:
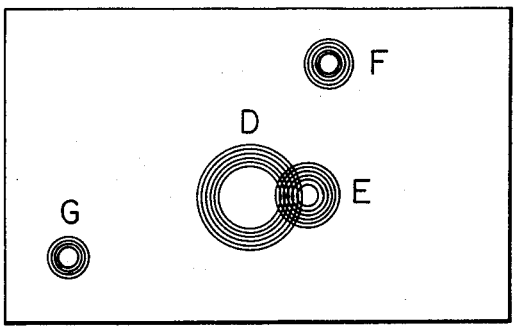
FIG. 10 is a diagrammatic view illustrating a thermal image of a difference in temperature which shows a thinned out portion, after elimination of a thermal image which shows a pseudo defective portion, in accordance with the method of the present invention.

In FIG. 9, "D", "E", "F" and "G" are portions of the thermal image, which show higher temperature caused by thinned out portions as defective portions on the inner surface 1b of the pipe 1. As is clear from showing the thinned out portion, to obtain a thermal image of the difference in temperature, which has only the portions "D", "E", "F" and "G" each showing the thinned out portion. FIG. 10 is a diagrammatic view illustrating the thus obtained thermal image of the difference in temperature, which shows only the thinned out portions as the defective portions.

Then, for each of the portions "D", "E", "F" and "G" showing the thinned out portions in the thermal image of the difference in temperature shown in FIG. 10, there is determined a temperature distribution of the thermal image of the difference in temperature on a line passing the highest temperature point of each portion. Subsequently, a differential value of the thus determined temperature distribution of each portion is calculated, and two points of inflection on the both sides of the highest temperature point of the temperature distribution are determined for each of the thinned out portion, on the basis of the thus calculated differential value of the temperature distribution. The presence and the extent of the thinned out portion are thus detected on the basis of a distance between the thus determined two points of inflection of the temperature distribution. Subsequently, the depth of the thinned out portion is detected on the basis of the detected highest temperature FIG. 9, the thus obtained thermal image of the difference in temperature of the outer surface of the pipe 1 includes the thermal image having the portions "A", "B" and "C" showing the pseudo defective portions on the paint film 1c on the outer surface of the pipe 1, in addition to the thermal image having the portions "D", "E", "F" and "G" showing the thinned out portions as the defective portions on the inner surface 1b of the pipe 1. The thus obtained thermal image of the difference in temperature having the portions "A", "B" and "C" showing the pseudo defective portions as well as the portions "D", "E", "F" and "G" showing the thinned out portions as the defective portions, is processed by means of an image processor not shown to obtain thermal image signals, and the thus obtained thermal image signals are entered into a memory not shown such as a video tape or a floppy disk.

Figure 14:
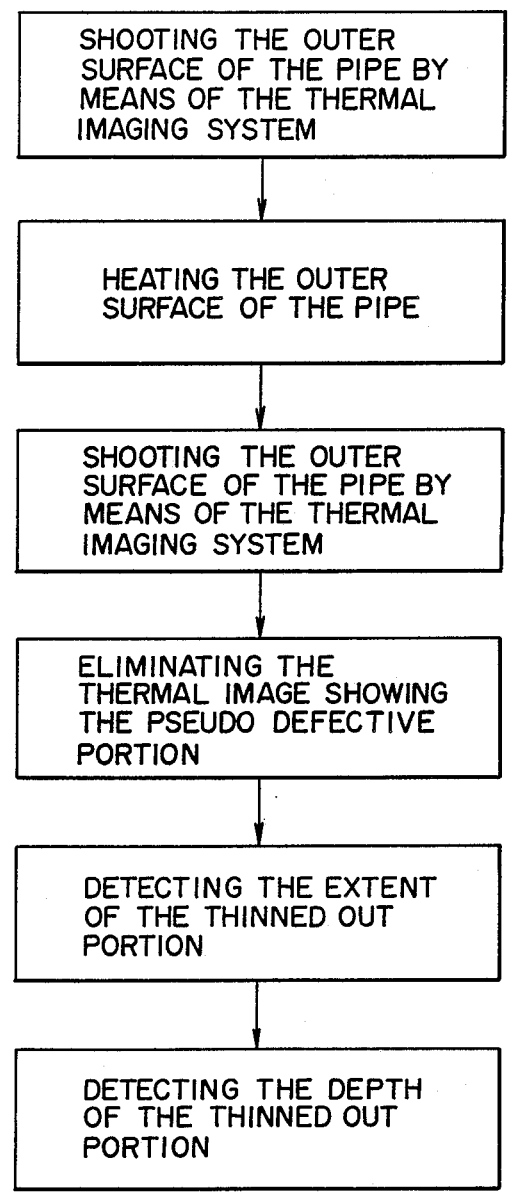
FIG. 14 is a block diagram illustrating typical steps of the method of the present invention.

Then, the thermal image signals obtained from the thermal image shown in FIG. 8, which has the portions "A", "B" and "C" each showing the pseudo defective portion, are eliminated from the thermal image signals obtained from the thermal image of the difference in temperature shown in FIG. 9, which has the portions "A", "B" and "C" each showing the pseudo defective portion as well as the portions "D", "E", "F" and "G" each point, the detected extent of the thinned out portion, and the previously determined heat analysis data. FIG. 14 is a block diagram illustrating the main steps of the above-mentioned third embodiment of the method of the present invention.

Now, a fourth embodiment of the method of the present invention is described below with reference to the drawings as to a case in which the thermal image showing a pseudo defective portion existing on the outer surface of a pipe, the outer surface of which is exposed, is first eliminated from the thermal image obtained by means of the thermal imaging system, and then the presence of a thinned out portion as a defective portion and an extent and/or a depth thereof on the inner surface of the pipe is detected.

As in the above-mentioned third embodiment, prior to heating a pipe 1 having a paint film 1c on the outer surface thereof and having a thinned out portion 2 as a defective portion on the inner surface 1b thereof from the side of the outer surface thereof or the inner surface thereof, the outer surface having the paint film 1c thereon of the pipe 1 is shot by means of a thermal image system 4 as shown in FIG. 7(A), to obtain a thermal image which has portions "A", "B" and "C" showing pseudo defective portions such as dirt and flaws on the paint film 1c. FIG. 8 is a diagrammatic view illustrating the thus obtained thermal image which shows the pseudo defective portions.

Figure 11:
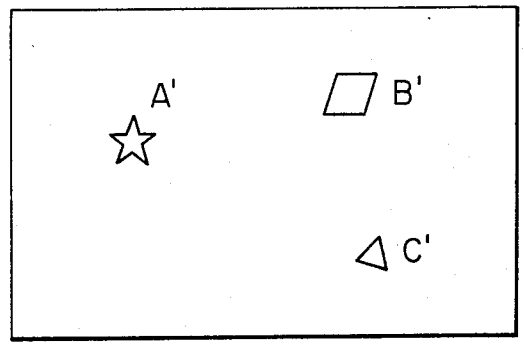
FIG. 11 is a diagrammatic view illustrating a thermal image which shows two points of inflection on the both sides of the highest temperature point of the temperature distribution of a pseudo defective portion, as determined in accordance with the method of the present invention.

Then, for each of the Portions "A", "B" and "C" showing the pseudo defective portions in the thermal image shown in FIG. 8, there is determined a temperature distribution of the thermal image on a line passing the highest temperature point of each portion. Subsequently, a differential value of the temperature distribution of each portion is calculated, and two points of inflection on the both sides of the highest temperature point of the temperature distribution are determined for the pseudo defective portion, on the basis of the thus calculated differential value of the temperature distribution. FIG. 11 is a diagrammatic view illustrating a thermal image which has portions "A'", "B'" and "C'" each showing two points of inflection thus determined on the both sides of the highest temperature point of the temperature distribution of the pseudo defective portion. The thus obtained thermal image which has the above-mentioned portions "A'", "B'" and "C'" each showing the pseudo defective portion, is processed by means of an image processor not shown to obtain thermal image signals, and the thus obtained thermal image signals are entered into a memory not shown such as a video tape or a floppy disk.

Then, in the same manner in the third embodiment as described above, the pipe 1 is heated from the side of the outer surface having the paint film 1c thereon of the pipe 1 by means of a heating mechanism 3 as shown in FIG. 7(B), so that a difference in temperature is produced between a portion of the outer surface of the pipe 1 corresponding to a thinned out portion 2 as a defective portion on the inner surface 1b of the pipe 1, on the one hand, and a portion of the outer surface of the pipe 1 corresponding to a normal portion of the inner surface 1b of the pipe 1, on the other hand. Then, while the above-mentioned difference in temperature still remains on the outer surface of the pipe 1, the outer surface of the pipe 1 is shot by means of the thermal imaging system 4 to obtain a thermal image of the difference in temperature, which has portions "A", "B" and "C" showing pseudo defective portions on the paint film 1c on the outer surface of the pipe 1, and portions "D", "E", "F" and "G" showing thinned out portions as defective portions on the inner surface 1b of the pipe 1. FIG. 9 is a diagrammatic view illustrating the thus obtained thermal image of the difference in temperature, which shows the pseudo defective portions and the thinned out portions.

Figure 12:
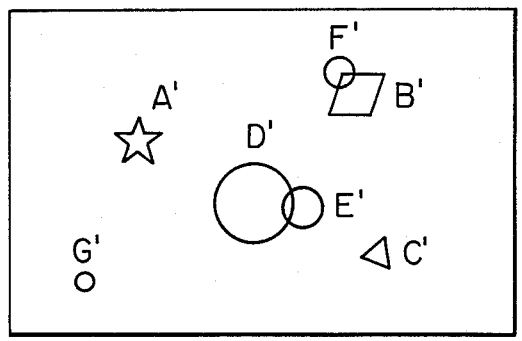
FIG. 12 is a diagrammatic view illustrating a thermal image which shows two points of inflection on the both sides of the highest temperature point of the temperature distribution of each of a pseudo defective portion and a thinned out portion, as determined in accordance with the method of the present invention.

Then, for each of the portions "A", "B" and "C" showing the pseudo defective portions and the portions "D", "E", "F" and "G" showing the thinned out portions in the thermal image of the difference in temperature shown in FIG. 9, there is determined a temperature distribution of the thermal image of the difference in temperature on a line passing the highest temperature point of each portion. Subsequently, a differential value of the thus determined temperature distribution of each portion is calculated, and two points of inflection on the both sides of the highest temperature point of the temperature distribution are determined for each of the pseudo defective portions and the thinned out portions, on the basis of the thus calculated differential value of the temperature distribution. FIG. 12 is a diagrammatic view illustrating a thermal image which has portions "A'", "B'" and "C'" each showing two points of inflection thus determined on the both sides of the highest temperature point of the temperature distribution of the pseudo defective portion as well as portions "D'", "E'", "F'" and "G'" each showing two points of inflection thus determined on the both sides of the highest temperature point of the temperature distribution of the thinned out portion. The thus obtained thermal image which has the above-mentioned portions "A'", "B'" and "C'" each showing the pseudo defective portions as well as the above-mentioned portions "D'", "E'", "F'" and "G'" each showing the thinned out portion, is processed by means of an image processor not shown to obtain thermal image signals, and the thus obtained thermal image signals are entered into a memory not shown such as a video tape or a floppy disk.

Figure 13:
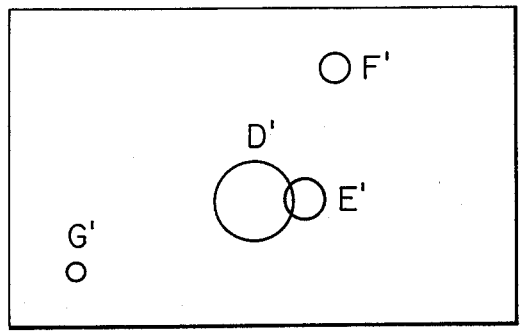
FIG. 13 is a diagrammatic view illustrating a thermal image which shows two points of inflection on the both sides of the highest temperature point of the temperature distribution of a thinned out portion, after elimination of a thermal image which shows two points of inflection on the both sides of the highest temperature point of the temperature distribution of a pseudo defective portion, in accordance with the method of the present invention.

Then, the thermal image signals obtained from the thermal image shown in FIG. 11, which has the portions "A'", "B'" and "C'" each showing the pseudo defective portion, are eliminated from the thermal image shown in FIG. 12, which has the portions "A'", "B'" and "C'" each showing the pseudo defective portion as well as the portions "D'", "E'", "F'" and "G'" each showing the thinned out portion, to obtain a thermal image which has only the portions "D'", "E'", "F'" and "G'" each showing the two points of inflection on the both sides of the highest temperature point of the temperature distribution of the thinned out portion. FIG. 13 is a diagrammatic view of the thermal image thus obtained, which shows the two points of inflection on the both sides of the highest temperature point of the temperature distribution of the thinned out portion, after elimination of the thermal image which shows the two points of inflection on the both sides of the highest temperature point of the temperature distribution of the pseudo defective portion.

The presence and the extent of the thinned out portion are thus detected on the basis of a distance between the two points of inflection of each of the portions "D'", "E'", "F'" and "G'" shown in FIG. 13. Subsequently, the depth of the thinned out portion is detected on the basis of the detected highest temperature point, the detected extent of the thinned out portion, and the previously determined heat analysis data.

According to the third and the fourth embodiments of the present invention, it is possible to eliminate the thermal image showing a pseudo defective portion existing on the inner surface of a pipe, the outer surface of which is not exposed, from the thermal image obtained by means of the thermal imaging system, and then to detect the presence of a thinned out portion and an extent and/or a depth thereof on the outer surface of the pipe.

All the steps of the above-mentioned first to fourth embodiments of the method of the present invention are continuously and mechanically carried out by a computer, thus permitting certain, easy and efficient detection of the presence of a thinned out portion as a defective portion and an extent and/or a depth thereof on the inner surface or the outer surface of the pipe.

Now, examples of the method of the present invention are described with reference to the drawings.

EXAMPLE 1

Five circular thinned out portions 2 having diameters of 50 mm, 40 mm, 30 mm, 20 mm and 10 mm, respectively, and a depth of 4 mm were formed on the inner surface 1b of a steel pipe 1 having an outside diameter of 165 mm and a thickness of 7 mm, as shown in FIG. 1, along the axial line of the pipe 1. The pipe 1 was heated from the side of the outer surface 1a thereof by means of a heating mechanism 3 so that a difference in temperature was produced between a portion of the outer surface 1a of the pipe 1 corresponding to each of the above-mentioned thinned out portions 2 on the inner surface 1b thereof, on the one hand, and a portion of the outer surface 1a of the pipe 1 corresponding to a normal portion of the inner surface 1b thereof, on the other hand. Then, while the above-mentioned difference in temperature still remained on the outer surface 1a of the pipe 1, the outer surface 1a of the pipe 1 was shot by means of a thermal imaging system 4 to obtain a thermal image of the difference in temperature showing the thinned out portions 2.

Figure 15:
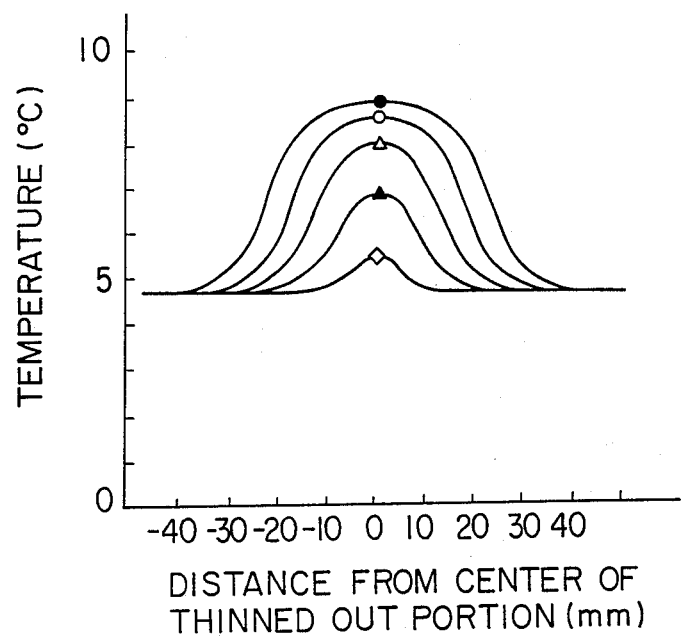
FIG. 15 is a graph illustrating a temperature distribution of a thermal image of the difference in temperature on a line passing the highest temperature point in the thermal image of the difference in temperature, which shows a thinned out portion, as determined in Example 1 of the method of the present invention.

Then, a temperature distribution of the thermal image of the difference in temperature on a line passing the highest temperature point in the thermal image of each of the thinned out portions 2 was determined. FIG. 15 is a graph illustrating the thus determined temperature distributions of the thermal image of the difference in temperature. In FIG. 15, the curve marked " ⇌ " represents the temperature distribution of the thinned out portion having a diameter of 50 mm; the curve marked "o" represents the temperature distribution of the thinned out portion having a diameter of 40 mm; the curve marked "Δ" represents the temperature distribution of the thinned out portion having a diameter of 40 mm; the curve marked " " represents the temperature distribution of the thinned out portion having a diameter of 20 mm; and the curve marked " " represents the temperature distribution of the thinned out portion having a diameter of 10 mm.

Figure 16:
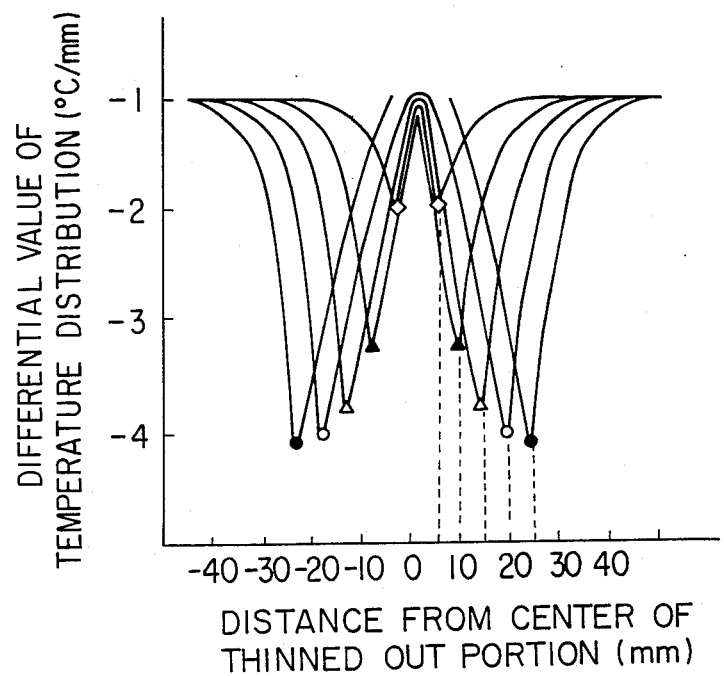
FIG. 16 is a graph illustrating a differential value of a temperature distribution of a thermal image, as calculated in Example 1 of the method of the present invention.

Then, a differential value of each of the above-mentioned temperature distributions was calculated, and two points of inflection on the both sides of the highest temperature point of the temperature distribution were determined for each of the thinned out portions, on the basis of the thus calculated differential value of the temperature distribution. FIG. 16 is a graph illustrating the thus calculated differential value of the temperature distribution of each of the thinned out portions. As is clear from FIG. 16, the two points of inflection on the both sides of the highest temperature point of the temperature distribution of each of the thinned out portions are situated respectively at a distance of 25 mm from the center of the thinned out portion for the temperature distribution marked " "; at a distance of 20 mm from the center of the thinned out portion for the temperature distribution marked "o"; at a distance of 15 mm from the center of the thinned out portion for the temperature distribution marked "Δ"; at a distance of 10 mm from the center of the thinned out portion for the temperature distribution marked " "; and at a distance of 5 mm from the center of the thinned out portion for the temperature distribution marked " ". More specifically, FIG. 16 shows that the thinned out portion marked " ⇌ " has a diameter 50 mm; the thinned out portion marked "o" has a diameter of 40 mm; the thinned out portion marked "Δ" has a diameter of 30 mm; the thinned out portion marked " " has a diameter of 20 mm; and the thinned out portion marked " " has a diameter of 10 mm.

Thus, the presence of the five circular thinned out portions 2 respectively having diameters of 50 mm, 40 mm, 30 mm, 20 mm and 10 mm was detected on the inner surface 1b of the pipe 1 along the axial line thereof, on the basis of the thus determined distance between the two points of inflection of the temperature distribution of each of the thinned out portions.

EXAMPLE 2

Five circular thinned out portions 2 having a diameter of 30 mm and thinning out ratios of 85%, 71%, 57%, 43% and 29%, respectively, were formed on the inner surface 1b of a steel pipe 1 of the same dimensions as in the Example 1 along the axial line thereof. As in the Example 1, the pipe 1 was heated from the side of the outer surface 1a thereof by means of a heating mechanism 3, and then, the outer surface 1a of the pipe 1 was shot by means of a thermal imaging system 4 to obtain a thermal image of the difference in temperature showing the thinned out portions 2.

Figure 17:
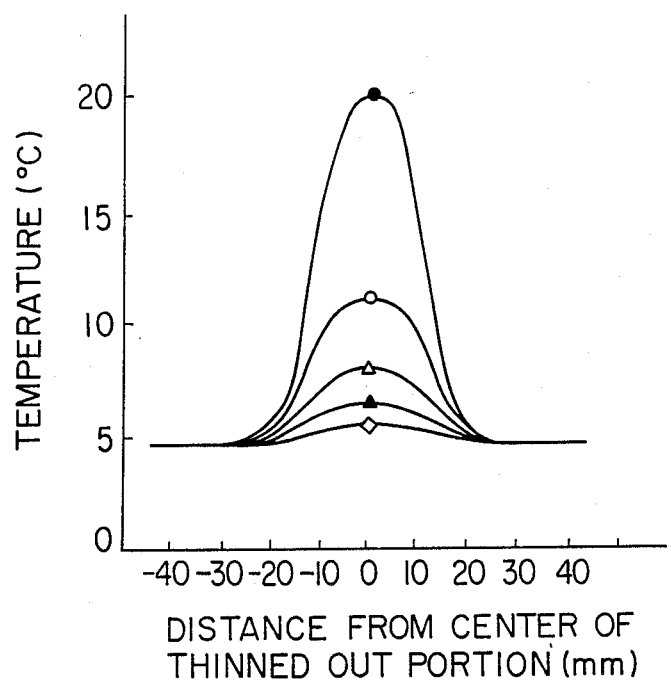
FIG. 17 is a graph illustrating a temperature distribution of a thermal image of the difference in temperature on a line passing the highest temperature point in the thermal image of the difference in temperature, which shows a thinned out portion, as determined in Example 2 of the method of the present invention.

Then, a temperature distribution of the thermal image of the difference in temperature on a line passing the highest temperature point in the thermal image of each of the thinned out portions 2 was determined. FIG. 17 is a graph illustrating the thus determined temperature distributions of the thermal images of the difference in temperature. In FIG. 17, the curve marked " " represents the temperature distribution of the thinned out portion having a thinning out ratio of 85%; the curve marked "o" represents the temperature distribution of the thinned out portion having a thinning out ratio of 71%; the curve marked "Δ" represents the temperature distribution of the thinned out portion having a thinning out ratio of 57%; the curve marked " " represents the temperature distribution of the thinned out having a thinning out ratio of 43%; and the curve marked " " represents the temperature distribution of the thinned out portion having a thinning out ratio of 29%.

Figure 18:
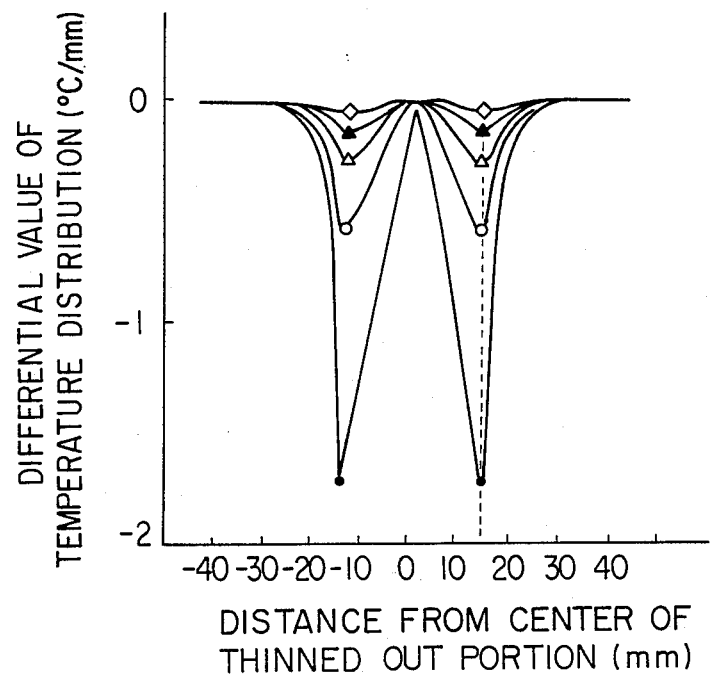
FIG. 18 is a graph illustrating a differential value of a temperature distribution of a thermal image, as calculated in Example 2 of the method of the present invention.

Then, a differential value of each of the above-mentioned temperature distributions was calculated, and two points of inflection on the both sides of the highest temperature point of the temperature distribution were determined for each of the thinned out portions, on the basis of the thus calculated differential value of the temperature distribution. FIG. 18 is a graph illustrating the thus calculated differential value of the temperature distribution of each of the thinned out portions. As is clear from FIG. 18, for the temperature distribution of any of the thinned out portions having the different thinning out ratios, the two points of inflection on the both sides of the highest temperature point of the temperature distribution of each of the thinned out portions are situated at a distance of 15 mm from the center of the thinned out portion. More specifically, FIG. 18 shows that all of the five thinned out portions 2 have a diameter of 30 mm.

Thus, the presence of the five circular thinned out portions 2 each having the diameter of 30 mm was detected on the inner surface 1b of the pipe 1 along the axial line thereof, on the basis of the distance between the two points of inflection of the temperature distribution of each of the thinned out portions.

In the method of the present invention, the material of the pipe to be tested may be any of metals such as steel, plastics, concrete, and any other materials. The method of the present invention is applicable irrespective of the cross-sectional shape and size of the pipe to be tested. Furthermore, the method of the present invention is not limited to the detection of a thinned out portion existing on the inner surface or the outer surface of the pipe, but is applicable to the detection of a thinned out portion on the inner surface of a side wall of a container, for example.

According to the present invention, as described above in detail, it is possible to certainly, easily and efficiently detect the presence of a thinned out portion as a defective portion and an extent and/or a depth thereof on the inner surface or the outer surface of a pipe, without the need for a special qualification, thus providing industrially useful effects.

What is claimed is:

1. In a method for detecting a thinned out portion on the inner surface or the outer surface of a pipe, which comprises the steps of:

heating or cooling a pipe to be tested from the side of the outer surface thereof or the inner surface thereof so that a difference in temperature is produced between (i) a portion of the outer surface or the inner surface of said pipe corresponding to a thinned out portion as a defective portion on the inner surface or the outer surface of said pipe, and (ii) a portion of the outer surface or the inner surface of said pipe corresponding to a normal portion of the inner surface or the outer surface of said pipe; then shooting the outer surface or the inner surface of said pipe by means of a thermal imaging system while said difference in temperature still remains on the outer surface or the inner surface of said pipe, to obtain a thermal image of said difference in temperature; and then detecting said thinned out portion of the inner surface or the outer surface of said pipe by means of the thus obtained thermal image;

the improvement comprising:

determining a temperature distribution of said thermal image of said difference in temperature on a line passing the highest temperature point or the lowest temperature point in said thermal image of said difference in temperature; then calculating a differential value of said temperature distribution; then determining two points of inflection on both sides of said highest temperature point or said lowest temperature point of said temperature distribution for said thinned out portion on the basis of said calculated differential value of said temperature distribution; and then detecting an extent of said thinned out portion on the basis of a distance between said two points of inflection of said temperature distribution.

2. In a method for detecting a thinned out portion on the inner surface or the outer surface of a pipe which comprises the steps of:

heating or cooling a pipe to be tested from the side of the outer surface thereof or the inner surface thereof so that a difference in temperature is produced between (i) a portion of the outer surface or the inner surface of said pipe corresponding to a thinned out portion as a defective portion on the inner surface or the outer surface of said pipe; and (ii) a portion of the outer surface or the inner surface of said pipe corresponding to a normal portion of the inner surface or the outer surface of said pipe; then shooting the outer surface or the inner surface of said pipe by means of a thermal imaging system while said difference in temperature still remains on the outer surface or the inner surface of said pipe, to obtain a thermal image of said difference in temperature; and then detecting said thinned out portion on the inner surface or the outer surface of said pipe by means of the thus obtained thermal image;

the improvement comprising:

determining a temperature distribution of said thermal image of said difference in temperature on a line passing the highest temperature point or the lowest temperature point in said thermal image of said difference in temperature; then calculating a differential value of said temperature distribution; then determining two points of inflection on both sides of said highest temperature point or said lowest temperature point of said temperature distribution for said thinned out portion on the basis of said calculated differential value of said temperature distribution; and then detecting an extent of said thinned out portion on the basis of a distance between said two points of inflection of said temperature distribution;

heating or cooling an experimental pipe having an artificial thinned out portion of a prescribed extent and a prescribed depth on the inner surface or the outer surface of said experimental pipe, from the side of the outer surface thereof or the inner surface thereof, to previously determine a heat analysis data concerning the relationship between (i) the highest temperature or the lowest temperature of a portion of the outer surface the inner surface of said experimental pipe corresponding to said artificial thinned out portion of the inner surface or the outer surface of said experimental pipe, (ii) the extent of said artificial thinned out portion, and (iii) the depth of said artificial thinned out portion; and then detecting a depth of said thinned out portion of said pipe to be tested on the basis of (i) said extent of said thinned out portion detected by said distance between said two points of inflection of said temperature distribution, (ii) said highest temperature point or said lowest temperature point in said thermal image of said difference in temperature, and (iii) said previously determined heat analysis data.

3. The method as claimed in claim 1, further comprising:

shooting, prior to said heating or said cooling of said pipe from the side of the outer surface thereof or the inner surface thereof, the outer surface or the inner surface of said pipe by means of said thermal imaging system, to obtain a thermal image which shows a pseudo defective portion including adhesion of foreign matters or presence of a thinned out portion on the outer surface or the inner surface of said pipe; then obtaining said thermal image of said difference in temperature, said thermal image of said difference in temperature including said thermal image showing said pseudo defective portion in addition to a thermal image showing said thinned out portion as said defective portion; then eliminating said thermal image showing said pseudo defective portion from said thermal image of said difference in temperature including said thermal image showing said pseudo defective portion; and then determining said temperature distribution of said thermal image of said difference in temperature from which said thermal image showing said pseudo defective portion has been eliminated.

4. The method as claimed in claim 1, further comprising:

shooting, prior to said heating or said cooling of said pipe from the side of the outer surface thereof or the inner surface thereof, the outer surface or the inner surface of said pipe by means of said thermal imaging system, to obtain a thermal image which shows a pseudo defective portion including adhesion of foreign matters or presence of a thinned out portion on the outer surface or the inner surface of said pipe; then determining a temperature distribution of said thermal image showing said pseudo defective portion on a line passing the highest temperature point or the lowest temperature point in said thermal image showing said pseudo defective portion; then calculating a differential value of said temperature distribution of said thermal image showing said pseudo defective portion; then determining two points of inflection on the both sides of said highest temperature point or said lowest temperature point of said temperature distribution for said pseudo defective portion, on the basis of said calculated differential value of said temperature distribution of said thermal image showing said pseudo defective portion; then obtaining said thermal image of said difference in temperature, said thermal image of said difference in temperature including said thermal image showing said pseudo defective portion in addition to a thermal image showing said thinned out portion as said defective portion; then determining a temperature distribution of each of said thermal image showing said pseudo defective portion and said thermal image showing said thinned out portion, on a line passing the highest temperature point or the lowest temperature point in said thermal image showing each of said pseudo defective portion and said thinned out portion, in said thermal image of said difference in temperature including said thermal image showing said pseudo defective portion; then calculating a differential value of each of said temperature distribution of said thermal image showing said pseudo defective portion and said temperature distribution of said thermal image showing said thinned out portion; then determining two points of inflection on the both sides of said highest temperature point or said lowest temperature point of said temperature distribution for each of said pseudo defective portion and said thinned out portion, on the basis of said calculated differential value of each of said temperature distribution of said thermal image showing said pseudo defective portion and said temperature distribution of said thermal image showing said thinned out portion; then eliminating said two points of inflection of said pseudo defective portion, as determined from said thermal image showing said pseudo defective portion, from said respective two points of inflection of said pseudo defective portion and said thinned out portion, as determined from said thermal image of said difference in temperature including said thermal image showing said pseudo defective portion; and then detecting an extent of said thinned out portion, on the basis of a distance between said two points of inflection of said thinned out portion thus obtained.

5. The method as claimed in claim 1, wherein:
the outer surface of said pipe is exposed; said thinned out portion exists on the inner surface of said pipe; said pipe is heated or cooled from the side of the outer surface thereof or the inner surface thereof; the outer surface of said pipe is shot by means of said thermal imaging system.

6. The method as claimed in claim 1, wherein:
the outer surface of said pipe is not exposed; said thinned out portion exists on the outer surface of said pipe; said pipe is heated or cooled from the side of the inner surface thereof; and the inner surface of said pipe is shot by means of said thermal imaging system.

7. The method as claimed in claim 2, further comprising:

shooting, prior to said heating or said cooling of said pipe from the side of the outer surface thereof or the inner surface thereof, the outer surface or the inner surface of said pipe by means of said thermal imaging system, to obtain a thermal image which shows a pseudo defective portion including adhesion of foreign matters or presence of a thinned out portion on the outer surface or the inner surface of said pipe; then obtaining said thermal image of said difference in temperature, said thermal image of said difference in temperature including said thermal image showing said pseudo defective portion in addition to a thermal image showing said thinned out portion as said defective portion; then eliminating said thermal image showing said pseudo defective portion from said thermal image of said difference in temperature including said thermal image showing said pseudo defective portion; and then determining said temperature distribution of said thermal image of said difference in temperature from which said thermal image showing said pseudo defective portion has been eliminated.

8. The method as claimed in claim 2, further comprising:

shooting, prior to said heating or said cooling of said pipe from the side of the outer surface thereof or the inner surface thereof, the outer surface or the inner surface of said pipe by means of said thermal imaging system, to obtain a thermal image which shows a pseudo defective portion including adhesion of foreign matters or presence of a thinned out portion on the outer surface or the inner surface of said pipe; then determining a temperature distribution of said thermal image showing said pseudo defective portion on a line passing the highest temperature point or the lowest temperature point in said thermal image showing said pseudo defective portion; then calculating a differential value of said temperature distribution of said thermal image showing said pseudo defective portion; then determining two points of inflection on the both sides of said highest temperature point or said lowest temperature point of said temperature distribution for said pseudo defective portion, on the basis of said calculated differential value of said temperature distribution of said thermal image showing said pseudo defective portion; then determining said thermal image of said difference in temperature, said thermal image of said difference in temperature including said thermal image showing said pseudo defective portion in addition to a thermal image showing said thinned out portion as said defective portion; then determining a temperature distribution of each of said thermal image showing said pseudo defective portion and said thermal image showing said thinned out portion, on a line passing the highest temperature point or the lowest temperature point in said thermal image showing each of said pseudo defective portion of said thinned out portion, in said thermal image of said difference in temperature including said thermal image showing said pseudo defective portion; then calculating a differential value of each of said temperature distribution of said thermal image showing said pseudo defective portion and said temperature distribution of said thermal image showing said thinned out portion; then determining two points of inflection on the both sides of said highest temperature point or said lowest temperature point of said temperature distribution for each of said pseudo defective portion and said thinned out portion, on the basis of said calculated differential value of each of said temperature distribution of said thermal image showing said pseudo defective portion and said temperature distribution of said thermal image showing said thinned out portion; then eliminating said two points of inflection of said pseudo defective portion, as determined from said thermal image showing said pseudo defective portion, from said respective two points of inflection of said pseudo defective portion and said thinned out portion, as determined from said thermal image of said difference in temperature including said thermal image showing said pseudo defective portion; and then detecting an extent of said thinned out portion, on the basis of a distance between said two points of inflection of said thinned out portion thus obtained.

9. The method as claimed in claim 2, wherein:
the outer surface of said pipe is exposed; said thinned out portion exists on the inner surface of said pipe; said pipe is heated or cooled from the side of the outer surface or the inner surface thereof and the outer surface of said pipe is shot by means of said thermal imaging system.

10. The method as claimed in claim 2, wherein:
the outer surface of said side is not exposed; said thinned out portion exists on the outer surface of said pipe; said pipe is heated or cooled from the side of the inner surface thereof; and the inner surface of said pipe is shot by means of said thermal imaging system.

* * * * *

UNITED STATES PATENT AND TRADEMARK OFFICE
CERTIFICATE OF CORRECTION

PATENT NO. : 4,983,836
DATED : January 8, 1991
INVENTOR(S) : MATOBA et al It is certified that error appears in the above-identified patent and that said Letters Patent is hereby corrected as shown below:

Column 17, line 21 (Claim 1, line 21):

change "of" to --on--.

Column 17, line 43 (Claim 2, line 2):

after "pipe", insert --,--.

Column 17, line 51 (Claim 2, line 10):

after "pipe", change ";" to --,--.

Column 18, line 8 (Claim 2, line 35):

after "portion", insert --,--.

Column 18, line 22 (Claim 2, line 49):

before "the inner", insert --or--.

Column 18, line 24 (Claim 2, line 51):

change "of" to --on--.

Column 20, line 1 (Claim 5, line 6):

before "the outer" , insert --and--.

Column 20, line 63 (Claim 8, line 27):

change "determining" to --obtaining--.

UNITED STATES PATENT AND TRADEMARK OFFICE
CERTIFICATE OF CORRECTION

PATENT NO. : 4,983,836

DATED : January 8, 1991

INVENTOR(S) : MATOBA et al

Page 2 of 2

It is certified that error appears in the above-identified patent and that said Letters Patent is hereby corrected as shown below:

```
Column 22, line 17 (Claim 9, line 5):

before "or", insert --thereof--.

Column 22, line 17 (Claim 9, line 5):

before "and", insert --,--.

Column 22, line 21 (Claim 10, line 2):

change "side" to --pipe--.
```

Signed and Sealed this

Third Day of November, 1992

Attest:

DOUGLAS B. COMER

Attesting Officer

Acting Commissioner of Patents and Trademarks